United States Patent [19]

Thunberg et al.

[11] 3,985,801

[45] Oct. 12, 1976

[54] PROCESS FOR RECOVERING GLYCINE FROM SODIUM CHLORIDE SOLUTIONS

[75] Inventors: Jon Carl Thunberg, Amherst, N.H.; Robert Wright Bragdon, Marblehead, Mass.; William Philip Moore, Hudson, N.H.

[73] Assignee: W. R. Grace & Co., New York, N.Y.

[22] Filed: Apr. 29, 1975

[21] Appl. No.: 572,860

Related U.S. Application Data

[63] Continuation-in-part of Ser. No. 517,469, Oct. 24, 1974, Pat. No. 3,904,585, which is a continuation-in-part of Ser. No. 442,543, Feb. 14, 1974, abandoned, which is a continuation-in-part of Ser. No. 319,539, Dec. 29, 1972, Pat. No. 3,808,269.

[52] U.S. Cl. .............................................. 260/534 R
[51] Int. Cl.² ........................................ C07C 99/12
[58] Field of Search ..................... 260/534 R, 534 C

[56] References Cited
UNITED STATES PATENTS

| | | | |
|---|---|---|---|
| 3,433,832 | 3/1969 | Swanson et al. | 260/534 S |
| 3,850,984 | 11/1974 | Selwitz | 260/534 E |

*Primary Examiner*—Vivian Garner
*Attorney, Agent, or Firm*—Elton Fisher

[57] ABSTRACT

Glycine can be recovered from an aqueous solution of glycine and sodium chloride having a mole ratio of glycine to sodium chloride of about 0.7–5:1 by: (a) adjusting the pH of the starting solution to 4.5–8.5 and evaporating water therefrom and cooling to precipitate glycine and to form a first mother liquor; (b) separating the precipitated glycine from the first mother liquor; and (c) recovering the separated glycine. Sodium chloride can be precipitated from the first mother liquor by evaporating water therefrom to form precipitated sodium chloride and a second mother liquor rich in glycine which can be separated from the precipitated sodium chloride and admixed with a second lot of the aqueous starting solution and processed therewith.

Alternatively, the sodium chloride can be precipitated and separated before precipitating the glycine by: (a) evaporating sufficient water to cause sodium chloride to precipitate from the hot solution (mother liquor); (b) separating the precipitated sodium chloride from the hot mother liquor; (c) cooling the separated mother liquor to cause glycine to precipitate; and (d) separating the precipitated glycine from the cooled mother liquor. The cooled separated mother liquor can be admixed with a second lot of the aqueous starting solution and processed therewith.

6 Claims, No Drawings

PROCESS FOR RECOVERING GLYCINE FROM SODIUM CHLORIDE SOLUTIONS

CROSS REFERENCE TO RELATED APPLICATIONS

This is a continuation-in-part of copending application Ser. No. 517,469, filed Oct. 24, 1974, and now U.S. Pat. No. 3,904,585. Said application Ser. No. 517,469 is a continuation-in-part of application Ser. No. 442,543, filed Feb. 14, 1974, and now abandoned. Said application Ser. No. 442,543 is a continuation-in-part of application Ser. No. 319,539, filed Dec. 29, 1972, and now U.S. Pat. No. 3,808,269. The benefit of said earlier filed applications is claimed.

BACKGROUND OF THE INVENTION

This invention is in the field of glycine. More specifically, this invention is directed to a process for preparing pure or substantially pure glycine.

In the prior art glycine was prepared by; (a) hydrolyzing the nitrile ($NH_2CH_2CN$) with an aqueous alkaline earth metal hydroxide to form an alkaline earth metal salt of the amino acid (glycine); and (b) treating the alkaline earth metal salt with carbon dioxide to form the free amino acid (which remains in solution) and an alkaline earth metal carbonate (which precipitates). The amino acid (glycine) was then recovered. This method, as applied to the preparation of glycine, is taught by U.S. Pat. No. 2,388,189 (Schweitzer, 260/534).

It is desirable to replace the alkaline earth metal hydroxide of the prior art with sodium hydroxide because the latter has a lower equivalent weight than strontium and barium hydroxides, is more soluble than the alkaline earth metal hydroxides, is easier to handle under plant conditions and the ions of sodium, unlike those of barium, (a preferred alkaline earth metal hydroxide) are not toxic. However, such substitution introduces a complication in the separation and recovery of the amino acid (glycine) because sodium carbonate, unlike the alkaline earth metal carbonates, is readily soluble in water, thereby to render the separation and recovery of pure or substantially pure glycine difficult.

A method for separating certain free amino acids from a system comprising the amino acid, sodium chloride, and water is taught by U.S. Pat. No. 3,433,832 (Swanson et al, 260/534).

The Swanson et al method is not applicable to an amino acid such as glycine which has a solubility greater than 35.0 parts per 100 parts of water at 100° C.

The process of our invention has been found to present an effective an convenient method for recovering glycine from a system consisting essentially of water, glycine and sodium chloride. Such a system results where glycine is formed from glycinonitrile by hydrolyzing said nitrile with sodium hydroxide and treating the resulting sodium glycinate with hydrochloric acid to convert the sodium salt (sodium glycinate) to the free amino acid (glycine). Our resulting aqueous glycine-sodium chloride solution generally contains at least about 5% glycine, and, if it does not, water can be evaporated therefrom to adjust the glycine concentration thereof to at least about 5% (by weight).

The solid components (glycine and sodium chloride) of the slurries formed in the process of our invention can be separated from the respective mother liquors by filtration, decantation, or centrifugation.

SUMMARY OF THE INVENTION

In summary, this invention is directed to a process for recovering glycine from an aqueous starting solution consisting essentially of water, glycine, and sodium chloride, the aqueous starting solution having a temperature above 0° (e.g., between about 0.5° C and about its normal boiling point or between about 5° and 100° C), a pH of 4.5–8.5, a mole ratio of glycine to sodium chloride of 0.7–5:1, or 1–5:1, or 0.7–3:1, or 0.9–2:1, the process comprising (or consisting essentially of):

a. forming a first slurry consisting essentially of a first lot of precipitated solid glycine and a first mother liquor consisting essentially of water, dissolved glycine, and dissolved sodium chloride by cooling the aqueous starting solution to a temperature effective for precipitating glycine (e.g., to a temperature within a range of about 0.5°–55° C, or 5°–50° C, or 10°–30° C, or to any temperature between about 0.5° and about 55° C) if the aqueous starting solution is above such temperature;

b. separating the first mother liquor from the first lot of precipitated solid glycine, and recovering the separated solid glycine;

c. forming a second slurry consisting essentially of a first lot of precipitated solid sodium chloride and a second mother liquor consisting essentially of water, dissolved glycine, and dissolved sodium chloride by evaporating water from the first mother liquor while maintaining the temperature of the resulting second slurry at a temperature effective for preventing the precipitation of solid glycine (e.g., within a temperature range between about 60° C and the normal boiling point of the second slurry (e.g., about 70°–100° C or 80°–95° C));

d. separating the second mother liquor from the first lot of precipitated solid sodium chloride while maintaining the temperature of the second slurry at a temperature effective for preventing the precipitation of solid glycine therein (e.g., within a temperature range between about 60° C and the normal boiling point of the second slurry (e.g., 70°–100° C or 80°–95° C));

e. forming a third slurry consisting essentially of a second lot of precipitated solid glycine and a third mother liquor consisting essentially of water, dissolved glycine, and dissolved sodium chloride by admixing the separated second mother liquor with a second lot of the aqueous starting solution and cooling the resulting admixture to a temperature effective for causing the second lot of solid glycine to precipitate from the aforesaid resulting admixture (e.g., to a temperature within the range of about 0.5°–55° C, or 5°–50° C, 10°–30° C, or to any temperature between about 0.5°– and about 55° C) if the resulting admixture is above such temperature;

f. separating the third mother liquor from the second lot of precipitated solid glycine and recovering the separated solid glycine;

g. forming a fourth slurry consisting essentially of a second lot of precipitated solid sodium chloride and a fourth mother liquor consisting essentially of water, dissolved glycine, and dissolved sodium chloride by evaporating water from the third mother liquor while maintaining the temperature of the resulting fourth slurry at a temperature effective for preventing the precipitation of solid glycine (e.g., within a temperature range between about 60° C and the normal boiling point of the second slurry (e.g., about 70°–100° C or 80°–95° C; and h. separating the fourth mother liquor from the second lot of precipitated solid sodium chloride while maintaining the temperature of the fourth slurry at a temperature effective for preventing the precipitation of solid glycine therein (e.g., within a temperature range between about 60° C and the normal boiling point of the second slurry (e.g., 70°–100° C or 80°–95° C)).

If the aqueous starting solution used in step (a) of this summary is so dilute that glycine does not precipitate on cooling, an evaporated system can be formed by evaporating from the aqueous starting solution an amount of water effective for causing glycine to precipitate when the evaporated system is cooled. The evaporated system can then be cooled to cause glycine to precipitate therefrom and to form the first slurry of this summary.

Steps (e), (f), (g), and (h), supra, can be repeated indefinitely by admixing the separated fourth mother liquor obtained in step (h) with a third (or subsequent) lot of starting aqueous solution (as recited in step (e)) and proceeding as recited in steps (e) through (h).

Where carrying on a long series of such runs (wherein steps (e) through (h) are repeated many times) it is generally preferred to remove a small portion of the fourth mother liquor (e.g., about 1–10% or 3–6% of the fourth mother liquor) to prevent the build up of color bodies and other undesired side-products which are present in small amounts in the starting aqueous solution. This removed portion is not admixed with starting aqueous solution in a repetition of step (e). It (the removed portion) can be discarded or processed separately to produce crude solid glycine which can be used as such or purified by conventional techniques such as recrystallization.

In steps (c) and/or (g) the evaporation can be conducted at temperatures (e.g., below about 55° or 60° C) at which glycine can be precipitated along with the sodium chloride during the evaporation step providing steps (d) and/or (h), respectively, are conducted at temperatures above about 60° C so that any glycine which precipitated in steps (c) or (g) is redissolved and is not separated from the mother liquor along with the precipitated solid sodium chloride.

DESCRIPTION OF PREFERRED EMBODIMENTS

In preferred embodiments of the process of the above Summary:

1. The pH of the starting solution is 4.5–8.5 or 5.5–6.5. If the pH of the first aqueous mixture is not within the desired range (4.5–8.5 or 5.5–6.5), it can be brought to this range by adding caustic soda or a sodium salt of the amino acid to increase the pH, or hydrochloric acid to lower the pH.

2. The mole ratio of glycine to sodium chloride in the aqueous starting solution is 0.9–2:1.

3. The aqueous starting solution analyzes about 21–25% glycine.

In the process of our invention it is preferred that at least a portion (e.g., up to about 80–99% or 95–97%) of separated fourth mother liquor from a previous run be admixed with the starting solution to form a resulting mixture which is cooled to precipitate crystalline glycine. This procedure can be continued for an unlimited number of runs, thereby to reduce or prevent loss of amino acid contained in the separated fourth mother liquor.

In another preferred embodiment ("Embodiment A") this invention is directed to a process for recovering glycine from an aqueous starting solution consisting essentially of water, glycine, and sodium chloride, the aqueous starting solution having a temperature above 0° C (e.g., between about 0.5° C and about its normal boiling point or between about 5° C and 100° C), a pH of 4.5–8.5, and a mole ratio of glycine to sodium chloride of 0.7–5:1, or 1–5:1 or 0.7–3:1, or 0.9–2:1, the process comprising (or consisting essentially of):

a. forming a first slurry consisting essentially of a first lot of precipitated solid sodium chloride and a first mother liquor consisting essentially of water, dissolved glycine, and dissolved sodium chloride by evaporating water from the aqueous starting solution;

b. separating the first mother liquor from the first lot of precipitated solid sodium chloride at a temperature effective for preventing the precipitation of solid glycine (e.g., within a temperature range between about 60° C and the normal boiling point of the second slurry (e.g., about 70°–100° C or 80°–95° C));

c. forming a second slurry consisting essentially of a first lot of precipitated solid glycine and a second mother liquor consisting essentially of water, dissolved glycine, and dissolved sodium chloride by adjusting the temperature of the separated first mother liquor to a temperature effective for precipitating glycine (e.g., to a temperature within a range of about 0.5°–55° C, or 5°–50° C, or 10°–30° C, or to any temperature between about 0.5° C and about 55° C) if the separated first mother liquor is above such temperature;

d. separating the second mother liquor from the first lot of precipitated solid glycine while maintaining the temperature of the second slurry within a temperature range effective for precipitating glycine (e.g., to a temperature within a range of about 0.5°–55° C, or 5°–50° C, or 10°–30° C, or to any temperature between about 0.5° C and about 55° C); and e. recovering the separated glycine.

In special embodiments of the process of Embodiment A, supra:

1. The pH of the aqueous starting solution is 4.5–8.5 or 5.5–6.5 If the pH of the starting solution is not within the desired range (4.5–8.5 or 5.5–6.5), it can be brought to this range by adding caustic soda or a sodium salt of the amino acid to increase the pH, or HCl to lower the pH.

2. The mole ratio of glycine to sodium chloride in the aqueous starting solution is 0.9–2:1.

3. The starting solution analyzes (contains) 20–45% glycine.

In another preferred embodiment, ("Embodiment B") this invention is directed to a process for recovering glycine from an aqueous starting solution consisting essentially of water, glycine, and sodium chloride, the aqueous starting solution having a temperature above 0° C (e.g., between about 0.5° C and about its normal boiling point or between about 5° C and 100° C), a pH of 4.5–8.5, and a mole ratio of glycine to sodium chloride of 0.7–5:1, or 1–5:1, or 0.7–3:1, or 0.9–2:1 the process comprising (or consisting essentially of):

a. forming a first slurry consisting essentially of a first lot of precipitated solid sodium chloride and a first mother liquor consisting essentially of water, dissolved glycine, and dissolved sodium chloride by evaporating water from the aqueous starting solution;

b. separating the first mother liquor from the first lot of precipitated solid sodium chloride at a temperature effective for preventing the precipitation of solid glycine (e.g., within a temperature range between about 60°C and the normal boiling point of the second slurry (e.g., about 70°–100° C or 80°–95° C));

c. forming a second slurry consisting essentially of a first lot of precipitated solid glycine and a second mother liquor consisting essentially of water, dissolved glycine, and dissolved sodium chloride by admixing the separated first mother liquor with a second lot of the aqueous starting solution, and adjusting the temperature of the resulting admixture to a temperature effective for precipitating glycine (e.g., to a temperature within a range of about 0.5°–55° C, or 5°–50° C, or 10°–30° C, or to any temperature between about 0.5° and about 55° C) if the separated first mother liquor is above such temperature;

d. separating the second mother liquor from the first lot of precipitated solid glycine while maintaining the temperature of the second slurry within a temperature range effective for precipitating glycine (e.g., to a temperature within a range of about 0.5°–55° C, or 5°–50° C, or 10°–30° C, or to any temperature between about 0.5° C and about 55° C);

e. forming a third slurry consisting essentially of a second lot of precipitated solid sodium chloride and a third mother liquor consisting essentially of water, dissolved glycine and dissolved sodium chloride by evaporating an amount of water effective for precipitating sodium chloride from the second mother liquor;

f. separating the third mother liquor from the second lot of precipitated solid sodium chloride at a temperature effective for preventing the precipitation of solid glycine (e.g., within a temperature range between about 60° C and the normal boiling point of the second slurry (e.g., about 70°–100° C or 80°–95° C));

g. forming a fourth slurry consisting essentially of a second lot of precipitated solid glycine and a fourth mother liquor consisting essentially of water, dissolved glycine, and dissolved sodium chloride by adjusting the temperature of the separated third mother liquor to a range effective for precipitating glycine (e.g., to a temperature within the range of about 0.5°–55° C, or 5°–50° C, 10°–30° C, or to any temperature between about 0.5° C and about 55° C); and h. separating the second lot of precipitated solid glycine from the fourth mother liquor at a temperature effective for precipitating glycine (e.g., to a temperature within a range of about 0.5°–55° C, or 5°–50° C, or 10°–30° C, or to any temperature between about 0.5° C and about 55° C).

Steps (e), (f), (g), and (h), supra, can be repeated indefinitely by admixing the separated fourth mother liquor obtained in step (h) with a third (or subsequent) lot of aqueous starting solution (as recited in step (e)) and proceeding as recited in steps (e) through (h).

Where carrying on a long series of such runs (wherein steps (e) through (h) are repeated many times) it is generally preferred to remove a small portion of the mother liquor (e.g., about 1–10% or 3–6% of the fourth mother liquor) to prevent the build up of color bodies, and other undesired side-products which are present in small amounts in the aqueous starting solution. This removed portion is not admixed with starting aqueous solution in a repetition of step (e). It (the removed portion) can be discarded or processed separately to produce crude solid glycine which can be used as such or purified by conventional techniques such as recrystallization.

In steps (a) and/or (e) the evaporation can be conducted at temperatures (e.g., below about 55° or 60° C) at which glycine can be precipitated along with the sodium chloride during the evaporation step providing steps (b) and/or (f), respectively, are conducted at temperatures above about 60° C so that any glycine which precipitated in steps (a) or (e) is redissolved and is not separated from the mother liquor along with the precipitated solid sodium chloride.

In certain embodiments of the invention of Embodiment B, supra:

1. The mole ratio of amino acid (glycine) to sodium chloride in the aqueous starting solution is 0.9–2:1.

2. The pH of the aqueous starting solution is 4.5–8.5 or 5.5–6.5. If the pH of the aqueous starting solution is not within the desired range (e.g., 4.5–8.5 or 5.5–6.5), it can be adjusted and brought within this range by methods which are within the skill of those of ordinary skill in the art (e.g., by adding hydrochloric acid to lower the pH or by adding NaOH or the sodium salt of glycine to increase the pH).

3. The separated third mother liquor or about 80–99% (preferably 95–97% thereof) is combined with separated first mother liquor from another run or with a fresh lot of the aqueous starting solution and the resulting mixture is processed.

4. The aqueous starting solution is prepared by reacting the sodium salt of the amino acid (glycine) with an amount of hydrochloric acid effective to convert the salt of the amino acid to free amino acid (glycine) and sodium chloride. The sodium salt of the amino acid is preferably prepared by reacting a nitrile ($H_2NCH_2CN$) corresponding to the amino acid ($H_2NCH_2COOH$) with an amount of aqueous sodium hydroxide solution effective for converting the nitrile to the sodium salt of the amino acid (glycine).

DETAILED DESCRIPTION OF THE INVENTION

If highly pure amino acid (glycine) is desired the recovered (product) amino acid can be dissolved in hot water and recrystallized therefrom by cooling to form a solid phase consisting essentially of the recrystallized amino acid and a liquid phase consisting essentially of a solution of the amino acid in water. The solid phase (amino acid) can be separated from the liquid phase and recovered. At least a portion (e.g., up to about 80–99%, or 90–98%, or 100%) of the liquid phase from which the solid phase was separated can be admixed with the water used to dissolve the amino acid in a subsequent run. Alternatively the liquid phase separated from the solid amino acid in this purification step can be admixed with the aqueous starting solution described in the above Summary or with the first mother liquor or the third mother liquor described in said Summary.

Because of our disclosure it will be readily apparent to those skilled in the art that water can be evaporated from the various solutions or slurries (from which water is evaporated in our process) at a reduced pressure (i.e., a pressure under 760 mm of mercury absolute) at normal atmospheric pressure, or at an elevated pressure (i.e., a pressure greater than 760 mm of mercury absolute). However, no particular advantage is gained by using reduced or elevated pressures and we generally prefer to operate at atmospheric pressure.

Because of our disclosure it will be readily understood by those skilled in the art that starting aqueous solutions containing considerably more than 5% amino acid (glycine) are preferred for use in the process of our invention because less water will have to be evaporated to cause the glycine to precipitate where using starting solutions containing appreciably more than 5% amino acid. Starting solutions containing about 20% or more of the amino acid are generally preferred. Obviously, starting solutions containing 1% or less amino acid can be used, but large amounts of water must be evaporated where using such solutions.

Aqueous slurries in which sodium chloride is present as a solid phase can be used in place of aqueous starting solutions. Where using such slurries we generally prefer to heat the slurry to a temperature effective to prevent the precipitation of the amino acid and to dissolve any precipitated amino acid before separating the solid sodium chloride. The mother liquor from which such solid sodium chloride has been separated can be used as starting solution in our process as recited in the above Summary. If necessary, additional water can be added to dissolve any solid amino acid present in such starting slurry.

A solution of glycine and sodium chloride which contains a low ratio of glycine to sodium chloride (e.g., a mole ratio of glycine to sodium chloride of 0.5:1 or less) can be converted to starting solution by evaporating water therefrom to precipitate crystalline sodium chloride and separating the precipitated sodium chloride at a temperature between about 60° C and the normal boiling point of the slurry (a slurry of solid sodium chloride in a mother liquor consisting essentially of water, dissolved glycine, and dissolved sodium chloride). Such mother liquor, after separating it from the precipitated sodium chloride, can be used as starting solution in the process described in the above Summary.

If the pH of the aqueous starting solution (i.e., the aqueous solution consisting essentially of water, amino acid, and sodium chloride) is not within a desired or preferred operating range (e.g., 4.5–8.5, 4.5–7, or 5.5–6.5), said pH can be adjusted before precipitating glycine therefrom. For example, hydrochloric acid can be added to lower the Ph and NaOH or sodium glycinate can be added to increase the pH. Further, if at any time the pH of a solution, slurry, or mother liquor is not within the desired operating range (e.g., 4.5–8.5, 4.5–7, or 5.5–6.5), such pH can be adjusted — e.g., by adding hydrochloric acid, or sodium hydroxide, or the sodium salt of glycine.

We prefer to prepare our amino acid (glycine) from glycinonitrile according to the following sequence of reactions:

$$H_2NCH_2CN + H_2O + NaOH = H_2NCH_2COONa + NH_3$$
$$H_2NCH_2COONa + HCl = H_2NCH_2COOH + NaCl$$

Where an excess of sodium hydroxide is added in the above saponification step sufficient hydrochloric acid is then added in the above acidification step to neutralize such excess (free) sodium hydroxide according to the following equation:

$$NaOH + HCl = NaCl + H_2O$$

The pH can be adjusted during (or after) the acidification step to a level (e.g., pH 4.5–8.5 or 5.5–6.5, or 6) preferred for separating the amino acid.

If too much hydrochloric acid is added during the acidification step or where adjusting the pH, the pH can be increased by neutralizing the excess acid with sodium hydroxide or with the sodium salt of the amino acid.

While it is preferred that the starting solution from which the amino acid (glycine) is recovered contain at least 5% amino acid, this value (5%) is not critical, and excellent results can be obtained with solutions containing less than about 5% of the amino acid. Solutions containing substantially less than 5% of the amino acid can be concentrated by evaporating water therefrom to bring their amino acid content to about 5%.

Because of our disclosure it will be readily apparent to those skilled in the art that if a slurry containing solid sodium chloride (or an aqueous starting solution containing such a high ratio of sodium chloride to glycine that sodium chloride precipitates before glycine on evaporating water from such solution) is used the precipitated sodium chloride should be separated before precipitating glycine. Dilution with water can, if required, be used in such a system to reduce or prevent the loss of glycine because the diluent water will dissolve either glycine or sodium chloride depending on the concentration before and after dilution and on the mole ratio of glycine to sodium chloride in the solution before and after such dilution.

In those instances where the sodium chloride is precipitated first, the separation of precipitated sodium chloride from the mother liquor is made at a temperature (e.g., above about 55° C or above about 60° C) effective for preventing the precipitation of glycine. Where glycine precipitates first the procedure of the above summary is followed and the separation of the precipitated glycine is made at a temperature below about 50° or 55° C.

In the process of our invention centrifugation, decantation, or filtration can be used to separate aqueous mother liquor from a precipitate (precipitated glycine or precipitated sodium chloride).

Glycine separated by the process of this invention can, if desired, be washed. For example, it can be washed with cool or cold water (e.g., water having the temperature of about 5°–25° C or up to about 30° C) or, alternatively with a solution of glycine (e.g., a saturated or nearly saturated aqueous solution of glycine). The solubility of glycine in water is 20.0% at 25° C, 23.0% at 35° C, and 36.1% at 80° C.

The instant invention will be better understood by referring to the following specific but nonlimiting procedures. It is understood that said invention is not limited by these procedures which are offered merely as illustrations; it is also understood that modification can be made without departing from the spirit and scope of the invention.

PROCEDURE 1

(Preparation of Aqueous Glycine-Sodium Chloride Solution)

A 50 mole portion of glycinonitrile is saponified at a temperature of about 50° C with 51 moles of sodium hydroxide supplied as an aqueous 20% sodium hydroxide solution. The saponified product is boiled free of ammonia, bleached with hydrogen peroxide (to remove undesirable side-product color bodies), and diluted with water to a total weight of 12.13 kilograms (Kg) to yield a 40% sodium glycinate solution. This solution is acidified with 51 moles of 36% hydrochloric acid solution to yield 17.30 Kg of an aqueous solution having a pH of about 6 and analyzing 21.7% glycine, 17.2% sodium chloride, and 61.1% water. This solution is designated "Solution 1".

Solution 1 is used as aqueous starting solution (i.e., the aqueous starting solution recited in the above Summary).

PROCEDURE 2

(Recovery of Glycine - First Cycle)

A 1,382 g portion of Solution 1 is boiled to evaporate water therefrom. When 182 g of water has been evaporated the heat source is removed and the resulting evaporated system is cooled to about 10° C and gently agitated (stirred) for about 2 hours to precipitate crystalline glycine and to form a first mother liquor. The first mother liquor and the precipitated crystalline glycine is separated (e.g., by centrifugation at about 10° C). The separated glycine which weighs 108 g is recovered.

The first mother liquor is boiled to evaporate water therefrom and to form a first slurry consisting essentially of a second mother liquor and precipitated crystalline sodium chloride. When about 411 g of water is evaporated the first slurry is cooled to about 80° C and the precipitated crystalline sodium chloride (117 g) is separated from the second mother liquor by centrifuging at about 80° C.

The separated second mother liquor is designated "Mother Liquor 2."

PROCEDURE 3

(Recovery of Glycine - Second Cycle)

All of Mother Liquor 2 is admixed with a second 1,382 g portion of Solution 1 to form a resulting mixture which is cooled to about 10° C to precipitate crystalline glycine therefrom and to form a third mother liquor. The precipitated glycine is separated from the third mother liquor by centrifuging at about 10° C. The separated crystalline glycine (189 g) is recovered.

The separated third mother liquor is boiled to evaporate water therefrom and to form a second slurry consisting essentially of a fourth mother liquor and separated crystalline sodium chloride. When about 693 g of water has been evaporated the second slurry is cooled to about 80° C and the precipitated sodium chloride (169 g) is separated from the fourth mother liquor by centrifuging at about 80° C. The separated fourth mother liquor (the separated final mother liquor) is designated Mother Liquor 3.

PROCEDURES 4 – 11

(Recovery of Glycine — 3rd-10th Cycles)

The general method of Procedure 3 is repeated in 8 subsequent replications (e.g., cycles 3–10). However, in these runs the method of Procedure 3 is modified by:

a. evaporating, in Cycles 3–10, the quantities of water listed in Table 1 from the respective third mother liquors (the respective mother liquors from which glycine has been precipitated in said cycles) to precipitate crystalline sodium chloride therefrom; and b. in Cycle 3 admixing separated fourth (final) mother liquor from the second cycle (i.e., Mother Liquor 3 from which sodium chloride had been separated in Cycle 2) and 1,382 g of Solution 1 to prepare the resulting mixture for use in this (third) cycle. Table 1 shows the grams of water evaporated from the respective third mother liquor (the respective mother liquors from which glycine has been precipitated in Cycles 3–10, Procedures 4–11).

In Procedures 5–11 (4th–10th cycles) the respective fourth mother liquors (i.e., the respective final mother liquors from respective previous cycles) are admixed with 1,382 g portions of starting Solution 1 to form the respective resulting mixtures for use in the respective cycles are as shown in Table 2.

TABLE 1

Water Evaporated from Respective Third Mother Liquors

| Procedure No. | Cycle No. | Water Evaporated, g |
|---|---|---|
| 4 | 3 | 779 |
| 5 | 4 | 784 |
| 6 | 5 | 809 |
| 7 | 6 | 793 |
| 8 | 7 | 821 |
| 9 | 8 | 793 |
| 10 | 9 | 805 |
| 11 | 10 | 816 |

TABLE 2

Final Mother Liquor Used in Procedures 4–11 (Cycles 3–10)

| Procedure No. | Cycle No. | Separated Final Mother Liquor Mixed with Solution 1 to Prepare Resulting Mixture |
|---|---|---|
| 5 | 4 | Final Mother Liquor from Procedure 4 |
| 6 | 5 | Final Mother Liquor from Procedure 5 |
| 7 | 6 | Final Mother Liquor from Procedure 6* |
| 8 | 7 | Final Mother Liquor from Procedure 7* |
| 9 | 8 | Final Mother Liquor from Procedure 8* |
| 10 | 9 | Final Mother Liquor from Procedure 9* |
| 11 | 10 | Final Mother Liquor from Procedure 10* |

*In each of Procedures 8, 9, 10, and 11 (Cycles 7, 8, 9, and 10) an amount of separated final mother liquor from the previous procedure containing about 19 g of glycine is discarded before mixing such final separated mother liquor with a 1,382g portion of Solution 1 to prepare resulting mixture for use in the next cycle (i.e., for use in Cycles 7, 8, 9, and 10, respectively).

Table 3 shows the amount of glycine and the amount of sodium chloride which is recovered in each of the above-described ten cycles (Procedures 2–11, Cycles 1–10).

TABLE 3

Glycine and Sodium Chloride Recovery

| Procedure No. | Cycle No. | Glycine Recovery g | NaCl Recovery g |
|---|---|---|---|
| 2 | 1 | 108 | 117 |
| 3 | 2 | 189 | 169 |
| 4 | 3 | 253 | 215 |
| 5 | 4 | 271 | 222 |
| 6 | 5 | 287 | 215 |
| 7 | 6 | 291 | 232 |
| 8 | 7 | 288 | 219 |
| 9 | 8 | 278 | 229 |
| 10 | 9 | 291 | 215 |
| 11 | 10 | 289 | 223 |
| | Total | 2,545* | 2,056* |

*These totals do not include 76 g of glycine and 47 g of NaCl discarded in the discarded portions of separated fourth mother liquor from Cycles 6, 7, 8, and 9 (which are discarded before preparing resulting mixture for use in Cycles 7, 8, 9, and 10). Neither do they include 363 g of glycine and 225 g of NaCl present in the separated final (fourth) mother liquor which is present at the end of Cycle 10. Such mother liquor (that obtained from Run 11 (Cycle 10)) or a portion of it can be used to prepare a resulting mixture for use in an eleventh cycle.

As shown in Table 3, total recovered glycine from Procedures 2 through 11, supra, (i.e., from Cycles 1-10, supra) is 2,545 g corresponding to a recovery of 84.8% of the glycine charged and the total recovered sodium chloride is 2,056 g. These totals are exclusive of the 76 g of glycine and 47 g of sodium chloride discarded (in separated fourth (final) mother liquors) in Procedures 7, 8, 9, and 10 (Cycles 6, 7, 8, and 9). These totals are also exclusive of the 363 g of glycine and 225 g of sodium chloride present in the separated fourth mother liquor at the end of Procedure 11 (Cycle 10). Including these excluded amounts in a balance sheet shows that 99.5% of the glycine charged in Cycles 1-10 and 97.8% of the sodium chloride charged in said Cycles 1-10 are accounted for.

PROCEDURE 12

(Preparation of Aqueous Glycine—Sodium Chloride Solution)

A second 17.30 Kg batch of Solution 1 can be prepared according to the method of Procedure 1.

PROCEDURE 13

(Recovery of Glycine — First Cycle)

A 1,382 g portion of the second batch of Solution 1 is boiled to evaporate water therefrom. When 462 g of water has been evaporated the temperature of the resulting slurry (solid crystallized (precipitated) sodium chloride and a first mother liquor) is adjusted to 80° C and the precipitated sodium chloride is separated therefrom, by centrifuging at 80° C, dried, and weighed (58 g).

The first mother liquor (860 g) from which the sodium chloride has been separated is combined with a fresh 1,382 g portion of said Solution 1. The resulting mixture is cooled to 10° C and stirred for 2 hours at 10° C to crystallize glycine. The thus formed slurry (glycine and a second mother liquor) is centrifuged at 10° C to separate the solid (crystallized or precipitated) glycine.

The separated glycine is recovered, dried, and weighed (243 g). The second mother liquor (1,989 g), which is also called "separated final mother liquor", is set aside for use in Procedure 14.

PROCEDURE 14

(Recovery of Glycine — Second Cycle)

All of the second mother liquor (the separated final mother liquor) from Procedure 13 is boiled to evaporate water therefrom and to crystallize (precipitate) sodium chloride. When 897 g of water has been evaporated the temperature of the resulting slurry is adjusted to 80° C and the precipitated sodium chloride is separated from the mother liquor (third mother liquor) by centrifuging at 80° C, dried and weighed (187 g).

The third mother liquor from which the sodium chloride has been separated is combined with 200 g of water and a 1,382 g portion of the second batch of Solution 1. The water is added to prevent sodium chloride from precipitating with glycine. The resulting mixture is cooled to 10° C to crystallize the glycine. The thus formed slurry (glycine and fourth mother liquor) is agitated (stirred) for two hours at 10° C and centrifuged at 10° C to separate the solid (precipitated) glycine. The separated glycine is recovered, dried and weighed (255 g). The fourth mother liquor, i.e., the separated final mother liquor, (2,213 g) is set aside for use in Procedure 15.

PROCEDURE 15

(Recovery of Glycine — Third Cycle)

All of the fourth mother liquor (separated final mother liquor) from Procedure 14 is boiled to evaporate water therefrom and to precipitate sodium chloride. When 836 g of water has been evaporated the temperature of the resulting slurry is adjusted to 80° C and the precipitated sodium chloride is separated from the mother liquor (fifth mother liquor) by centrifuging at 80° C, dried, and weighed (227 g).

The fifth mother liquor from which the sodium chloride has been separated is combined with a 1,382 g portion of the second batch of Solution 1. The resulting mixture is cooled to 10° C to crystallize glycine, stirred for two hours at 10° C, and centrifuged for two hours to separate the precipitated glycine from the sixth mother liquor from which it (the precipitated glycine) had precipitated. The separated glycine is recovered, dried, and weighed (297 g). The sixth mother liquor, i.e., the separated final mother liquor, (2,207 g) is set aside for use in Procedure 16.

PROCEDURES 16-22

(Recovery of Glycine — 4-10 Cycles)

The general method of Procedure 15 is repeated in 7 subsequent replications (i.e., Cycles 4-10). However, in these runs the method of Procedure 15 is modified by:

a. evaporating the respective quantities of water listed in Table 4 from the respective separated final mother liquors to precipitate sodium chloride therefrom and separating (preferably by centrifugation) the precipitated sodium chloride at about 80° C; and b. in each cycle (except Cycle 10, Procedure 22) admixing a 1,382 g portion of the second batch of Solution 1 with at least a portion of the mother liquor from which precipitated sodium chloride has been separated in the same cycle to form a resulting solution from which glycine will be precipitated by cooling;

i. the thus formed resulting solution is, in each cycle, cooled to precipitate glycine is separated by centrifugation at about 10° C; the separated glycine is recovered, dried, and weighed;

ii. in each instance (except Cycle 10) the mother liquor from which the precipitated glycine has been separated is a separated final solution which is evaporated in the next cycle to precipitate sodium chloride; and iii. in Cycle 10 the mother liquor from which precipitated sodium chloride has been separated is admixed with 185 g of water (but not with any of the second batch of Solution 1) to form a resulting mixture from which glycine is precipitated by cooling.

Table 4 shows the grams of water evaporated from the respective separated final mother liquors from the respective previous cycles in Cycles 4-10 (Procedures 16-22).

TABLE 4

| Water Evaporated from Separated Final Mother Liquors | | |
|---|---|---|
| Procedure No. | Cycle No. | Water Evaporated, g |
| 16 | 4 | 820 |
| 17 | 5 | 817 |
| 18 | 6 | 827 |

TABLE 4-continued

Water Evaporated from Separated Final Mother Liquors

| Procedure No. | Cycle No. | Water Evaporated, g |
|---|---|---|
| 19 | 7 | 884 |
| 20 | 8 | 879 |
| 21 | 9 | 874 |
| 22 | 10 | 862 |

Table 5 shows the respective final mother liquors used in Cycles 4–10 (Procedures 16–22).

TABLE 5

Respective Separated Final Mother Liquors Used In Procedures 17–22 (Cycles 5–10)

| Procedure No. | Cycle No. | Separated Final Mother Liquor Used |
|---|---|---|
| 16 | 4 | From Procedure 15 |
| 17 | 5 | From Procedure 16 |
| 18[a] | 6 | From Procedure 17 |
| 19[a] | 7 | From Procedure 18 |
| 20[a] | 8 | From Procedure 19 |
| 21[a] | 9 | From Procedure 20 |
| 22 | 10 | From Procedure 21 |

[a] In each of Procedures 18, 19, 20, and 21 (Cycles 6, 7, 8, and 9) an amount of separated final mother liquor from the previous procedure (previous cycle) containing about 18 g of glycine is discarded before evaporating water from such mother liquor to precipitate sodium chloride therefrom. This prevents the build up of undesirable color bodies and any other possible undesirable side products such as IDA.

Table 6 shows the amount of glycine and the amount of sodium chloride which is recovered in each of the above-described ten cycles (Procedures 13–22, Cycles 1–10).

TABLE 6

Glycine and Sodium Chloride Recovery

| Procedure No. | Cycle No. | Glycine Recovery g | NaCl Recovery g |
|---|---|---|---|
| 13 | 1 | 243 | 58 |
| 14 | 2 | 255 | 187 |
| 15 | 3 | 297 | 227 |
| 16 | 4 | 300 | 228 |
| 17 | 5 | 299 | 244 |
| 18 | 6 | 299 | 229 |
| 19 | 7 | 293 | 228 |
| 20 | 8 | 289 | 225 |
| 21 | 9 | 286 | 220 |
| 22 | 10 | 93 | 223 |
| | Total | 2,654* | 2,069* |

*These totals do not include 72 g of glycine and 88 g of sodium chloride discarded in portions of separated final mother liquor (mother liquor from which precipitated glycine has been separated) before evaporating water therefrom to precipitate sodium chloride in Cycles 6, 7, 8, and 9 (Procedures 18–21). Neither do they include 268 g of glycine and 216 g of sodium chloride present in the separated final mother liquor which is present at the end of Cycle 10 (Procedure 22). Said separated final mother liquor (that obtained from Cycle 10 (Procedure 22) or a portion thereof can be used in an eleventh cycle.

All glycine charged and all sodium chloride charged are accounted for.

88.5% of the glycine charged was actually recovered as crystallized glycine in Procedures 13–22 (Cycles 1–10).

Glycine is an article of commerce. It is useful as an additive in metal plating baths, as a nutrient supplement for animal feeds and fermentation broths, and as a flavor enhancing agent in food.

As used herein the term "percent (%)" means parts per hundred and parts means parts by weight unless otherwise defined where used.

As used herein the term "mole" has its generally accepted meaning. A mole of a substance is that quantity which contains the same number of molecules of the substance as there are atoms in 12 grams of pure $^{12}C$.

As used herein the term "g" means gram or grams and the term "Kg" means kilogram or kilograms. A kilogram is 1,000 grams.

As used herein the term "IDA" means iminodiacetic acid.

We claim,

1. A process for recovering glycine from an aqueous starting solution consisting essentially of water, glycine, and sodium chloride, the aqueous starting solution having a temperature above 0° C, a pH of 4.5–8.5, a mole ratio of glycine to sodium chloride of 0.7–5:1, the process comprising:
    a. forming a first slurry consisting essentially of a first lot of precipitated glycine and a first mother liquor consisting essentially of water, dissolved glycine, and dissolved sodium chloride by cooling the aqueous starting solution to a temperature effective for precipitating glycine;
    b. separating the first mother liquor from the first lot of precipitated glycine, and recovering the separated solid glycine;
    c. forming a second slurry consisting essentially of a first lot of precipitated sodium chloride and a second mother liquor consisting essentially of water, dissolved glycine, and dissolved sodium chloride by evaporating water from the first mother liquor;
    d. separating the second mother liquor from the first lot of precipitated sodium chloride while maintaining the temperature of the second slurry at a temperature effective for preventing the precipitation of glycine;
    e. forming a third slurry consisting essentially of a second lot of precipitated glycine and a third mother liquor consisting essentially of water, dissolved glycine, and dissolved sodium chloride by admixing the separated second mother liquor with a second lot of the aqueous starting solution and cooling the resulting admixture to a temperature effective for causing the second lot of glycine to precipitate;
    f. separating the third mother liquor from the second lot of precipitated solid glycine and recovering the separated solid glycine;
    g. forming a fourth slurry consisting essentially of a second lot of precipitated sodium chloride and a fourth mother liquor consisting essentially of water, dissolved glycine, and dissolved sodium chloride by evaporating water from the third mother liquor; and
    h. separating the fourth mother liquor from the second lot of precipitated sodium chloride while maintaining the temperature of the fourth slurry at a temperature effective for preventing the precipitation of solid glycine.

2. The process of claim 1 in which the pH of the aqueous starting solution is 5.5–6.5.

3. The process of claim 1 in which the mole ratio of glycine to sodium chloride in the aqueous starting solution is 0.9–2:1.

4. The process of claim 1 in which the aqueous starting solution analyzes about 21–25% glycine.

5. The process of claim 1 in which the aqueous starting solution is prepared by reacting sodium glycinate with an amount of hydrochloric acid effective to convert the sodium glycinate to free glycine and sodium chloride.

6. The process of claim 5 in which sodium glycinate is prepared by reacting glycinonitrile with an aqueous sodium hydroxide solution.

* * * * *